US012279758B2

(12) United States Patent
Abbas et al.

(10) Patent No.: US 12,279,758 B2
(45) Date of Patent: Apr. 22, 2025

(54) TISSUE DETECTION SYSTEMS AND METHODS

(71) Applicant: AI Biomed Corp., Santa Barbara, CA (US)

(72) Inventors: Adnan S. Abbas, Santa Barbara, CA (US); Nicholas F. Pergola, Arvada, CO (US)

(73) Assignee: AI Biomed Corp., Santa Barbara, CA (US)

(*) Notice: Subject to any disclaimer, the term of this patent is extended or adjusted under 35 U.S.C. 154(b) by 0 days.

(21) Appl. No.: 17/486,719

(22) Filed: Sep. 27, 2021

(65) Prior Publication Data

US 2023/0103605 A1 Apr. 6, 2023

(51) Int. Cl.
*A61B 1/07* (2006.01)
*A61B 1/00* (2006.01)
(Continued)

(52) U.S. Cl.
CPC ............ *A61B 1/07* (2013.01); *A61B 1/00096* (2013.01); *A61B 1/046* (2022.02); *A61B 1/0646* (2013.01);
(Continued)

(58) Field of Classification Search
CPC . A61B 1/00096; A61B 1/00186; A61B 1/043; A61B 1/051; A61B 1/0646; A61B 1/07
See application file for complete search history.

(56) References Cited

U.S. PATENT DOCUMENTS

| 5,749,830 A | * | 5/1998 | Kaneko | A61B 1/0638 348/E5.038 |
| 5,956,136 A | * | 9/1999 | Da Silva | G01J 3/12 356/417 |

(Continued)

FOREIGN PATENT DOCUMENTS

| CN | 106901679 A | * | 6/2017 |
| CN | 113017854 A | | 6/2021 |

(Continued)

OTHER PUBLICATIONS

Partial European Search Report and Provisional Opinion issued in corresponding application EP 22196569.2 dated Feb. 27, 2023 (14 pages).

(Continued)

*Primary Examiner* — John P Leubecker
(74) *Attorney, Agent, or Firm* — Carter, DeLuca & Farrell LLP

(57) ABSTRACT

A tissue detection system includes a probe having a body defining a distal end portion for positioning in contact with or close proximity to tissue. The probe includes an emission optical fiber extending from an input end through the probe body to an output end at the distal end portion of the probe body, and a detection optical fiber extending from an output end through the probe body to an input end at the distal end portion of the probe body. An emitter is coupled to the input end of the emission optical fiber and a detector is coupled to the output end of the detection optical fiber. One or more optical elements is disposed at the detector filter out electromagnetic radiation received from the detection optical fiber below a pre-determined wavelength threshold or outside of a pre-determined wavelength range.

18 Claims, 7 Drawing Sheets

(51) Int. Cl.
*A61B 1/04* (2006.01)
*A61B 1/06* (2006.01)
*A61B 5/00* (2006.01)

(52) U.S. Cl.
CPC ......... *A61B 1/00186* (2013.01); *A61B 5/0059* (2013.01); *A61B 5/0071* (2013.01)

(56) References Cited

U.S. PATENT DOCUMENTS

| | | | |
|---|---|---|---|
| 6,470,124 B1* | 10/2002 | Le Gargasson | A61B 1/00165 385/117 |
| 8,364,246 B2 | 1/2013 | Thierman | |
| 9,687,190 B2 | 6/2017 | Mahadevan-Jansen et al. | |
| 10,579,891 B2 | 3/2020 | Abbas et al. | |
| 2002/0033989 A1* | 3/2002 | Fisher | A61K 49/0017 359/278 |
| 2002/0044279 A1 | 4/2002 | Khoury | |
| 2002/0099293 A1* | 7/2002 | Fontenot | A61B 1/3132 600/478 |
| 2002/0177778 A1 | 11/2002 | Averback et al. | |
| 2003/0229270 A1* | 12/2003 | Suzuki | A61B 5/0084 600/178 |
| 2006/0247537 A1* | 11/2006 | Matsumoto | A61B 5/0084 600/478 |
| 2007/0203413 A1* | 8/2007 | Frangioni | A61B 1/042 600/478 |
| 2008/0004533 A1 | 1/2008 | Jansen et al. | |
| 2009/0141271 A1* | 6/2009 | Matousek | G01N 21/65 356/301 |
| 2009/0177043 A1* | 7/2009 | Akiyama | A61B 5/0084 600/181 |
| 2011/0237895 A1* | 9/2011 | Yoshida | A61B 1/063 600/180 |
| 2011/0280810 A1* | 11/2011 | Hauger | G02B 21/0052 424/9.6 |
| 2012/0010483 A1* | 1/2012 | Mahadevan-Jansen | A61B 5/4227 600/310 |
| 2012/0268573 A1* | 10/2012 | Schonborn | A61B 1/00009 348/E13.074 |
| 2013/0216482 A1 | 8/2013 | Kwon et al. | |
| 2014/0340500 A1 | 11/2014 | Hoegele | |
| 2015/0216398 A1* | 8/2015 | Yang | A61B 1/000094 600/109 |
| 2015/0374452 A1 | 12/2015 | Saito | |
| 2016/0313183 A1 | 10/2016 | Teraoka et al. | |
| 2017/0046586 A1* | 2/2017 | Abbas | G06V 10/141 |
| 2017/0232119 A1 | 8/2017 | Kularatne et al. | |
| 2017/0236022 A1* | 8/2017 | Abbas | A61B 90/361 348/77 |
| 2019/0298151 A1* | 10/2019 | Frangioni | A61B 1/046 |
| 2020/0284657 A1* | 9/2020 | Leblond | G01J 3/0227 |
| 2020/0305696 A1 | 10/2020 | Abbas et al. | |
| 2021/0338308 A1 | 11/2021 | Pergola et al. | |

FOREIGN PATENT DOCUMENTS

| | | |
|---|---|---|
| EP | 2838415 A1 | 2/2015 |
| EP | 3005941 A2 | 4/2016 |
| WO | 2004075032 A2 | 9/2004 |
| WO | 2009052466 A1 | 4/2009 |

OTHER PUBLICATIONS

Extended European Search Report issued in corresponding application EP 22196569.2 dated Jun. 29, 2023 (14 pages).

* cited by examiner

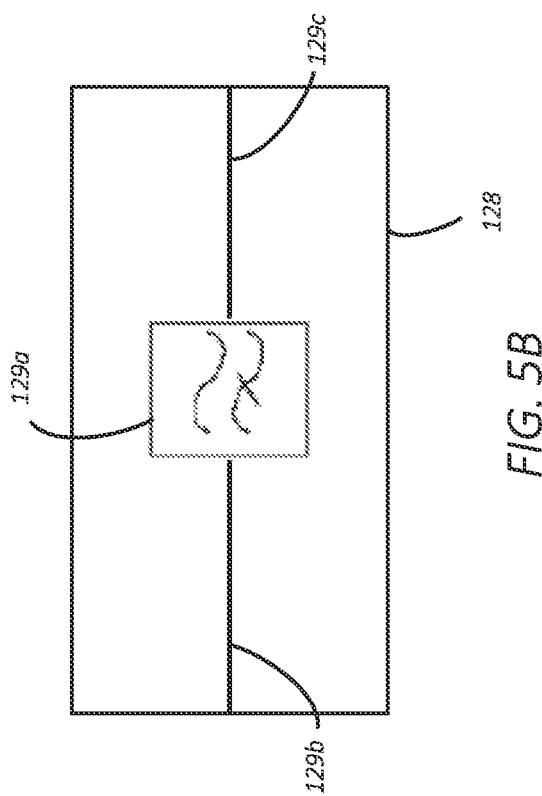
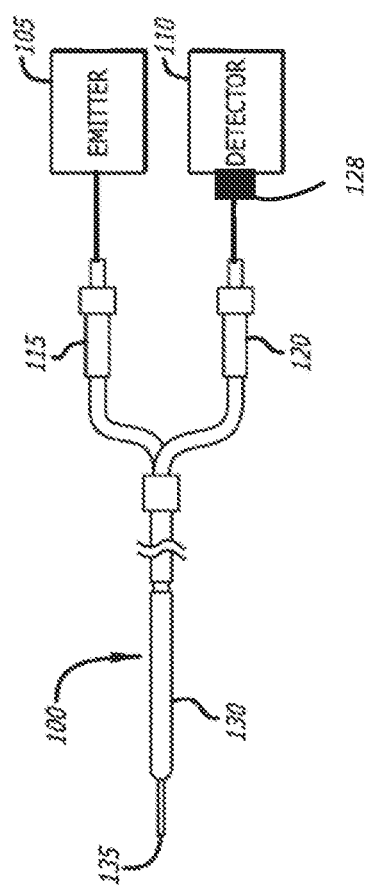
FIG. 5B
FIG. 5A

TISSUE DETECTION SYSTEMS AND METHODS

BACKGROUND

Technical Field

The present disclosure relates to tissue detection and, more particularly, to systems and methods facilitating detection of tissue of interest at a surgical site.

Background of Related Art

Many surgical procedures are performed at surgical sites on or within the body where the detection of tissue of interest via direct visualization techniques alone (e.g., using the human eye, a lens-based endoscope, a surgical video camera, etc.) is difficult due to obstructions, darkness, minimal or no contrast between different tissues, minimal or no visible distinction between different tissues, etc. Such surgical procedures may thus benefit from the use of enhanced visualization techniques such as, for example, fluorescence.

Since some materials, including certain tissues, fluoresce when stimulated with electromagnetic radiation (e.g., light at non-visible wavelengths), fluorescence can be used to highlight tissue of interest, thus facilitating detection of tissue of interest that may otherwise be difficult or impossible to detect solely by direct visualization techniques. The particular wavelength or wavelengths of electromagnetic radiation emitted and detected may depend upon the tissue or tissues of interest to be highlighted.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent. The term "tissue," as utilized herein, is broadly defined to include bodily material including, without limitation, connective tissue, epithelial tissue muscle tissue, nervous tissue, and/or any other bodily material whether a solid, semi-solid fluid, etc. Further, to the extent consistent, any or all of the aspects detailed herein may be used in conjunction with any or all of the other aspects detailed herein.

Provided in accordance with aspects of the present disclosure is a tissue detection system including a probe, an emitter, a detector, and one or more optical elements. The probe has a probe body defining a distal end portion configured for positioning in contact with or close proximity to tissue of interest. The probe further includes an emission optical fiber extending from an input end of the emission optical fiber through the probe body to an output end of the emission optical fiber at the distal end portion of the probe body, and a detection optical fiber extending from an output end of the detection optical fiber through the probe body to an input end of the detection optical fiber at the distal end portion of the probe body. The emitter is coupled to the input end of the emission optical fiber and the detector is coupled to the output end of the detection optical fiber. The one or more optical elements is disposed at the detector and configured to filter out electromagnetic radiation received from the detection optical fiber below a pre-determined wavelength threshold or outside of a pre-determined wavelength range.

In an aspect of the present disclosure, the one or more optical elements includes a Long-Pass (LP) filter.

In another aspect of the present disclosure, the one or more optical elements is configured to filter out electromagnetic radiation below the pre-determined wavelength threshold of about 800 nm.

In still another aspect of the present disclosure, the one or more optical elements is configured to filter out electromagnetic radiation outside of the pre-determined wavelength range of about 808 to about 1000 nm.

In yet another aspect of the present disclosure, the probe does not include a filter disposed on an input side of the detection optical fiber.

In still yet another aspect of the present disclosure, the emitter is configured to input electromagnetic radiation to the input end of the emission optical fiber at a wavelength of about 785 nm.

In another aspect of the present disclosure, the one or more optical elements and the detector are disposed within a console.

Another tissue detection system provided in accordance with aspects of the present disclosure includes a probe having a probe body defining a distal end portion configured for positioning in contact with or close proximity to tissue of interest. The probe further includes an emission optical fiber extending from an input end of the emission optical fiber through the probe body to an output end of the emission optical fiber at the distal end portion of the probe body, and a detection optical fiber extending from an output end of the detection optical fiber through the probe body to an input end of the detection optical fiber at the distal end portion of the probe body. An emitter is coupled to the input end of the emission optical fiber and a detector includes an input that is coupled to the output end of the detection optical fiber. First and second filters are disposed at the input end of the detection optical fiber or at the input of the detector in series with one another. The first and second filters define an angle therebetween.

In an aspect of the present disclosure, the first and second filters are each Long-Pass (LP) filters.

In another aspect of the present disclosure, at least one of the first or second filters is angled relative to an optical axis of the detection optical fiber or the detector. In aspects, both of the first and second filters are angled relative to the optical axis.

In still another aspect of the present disclosure, the first and second filters define a collective Optical Density (OD) of at least about 9 without any one of the first or second optical filters defining an individual OD of more than about 6. Further, in aspects, the first and second filters define a collective OD of at least about 12 without any one of the first or second optical filters defining an individual OD of more than about 6.

In yet another aspect of the present disclosure, the first and second filters are configured to filter out electromagnetic radiation below a pre-determined wavelength threshold of about 800 nm or outside of a pre-determined wavelength range of about 808 to about 1000 nm.

Still another tissue detection system provided in accordance with the present disclosure includes a probe having a probe body defining a distal end portion configured for positioning in contact with or close proximity to tissue of interest. The probe includes an emission optical fiber extending from an input end of the emission optical fiber through the probe body to an output end of the emission optical fiber at the distal end portion of the probe body, and a detection optical fiber extending from an output end of the detection optical fiber through the probe body to an input end of the detection optical fiber at the distal end portion of the probe body. An emitter is coupled to the input end of the emission optical fiber and a detector includes an input that is coupled to the output end of the detection optical fiber. A filter is disposed at the input end of the detection optical fiber or at the input of the detector and defines an Optical Density (OD) of at least about 9 or, in aspects, of at least about 12.

In an aspect of the present disclosure, the filter is a Long-Pass (LP) filter.

In another aspect of the present disclosure, the filter is configured to filter out electromagnetic radiation below a pre-determined wavelength threshold of about 800 nm or outside of a pre-determined wavelength range of about 808 to about 1000 nm.

Also provided in accordance with aspects of the present disclosure is a tissue detection system including a probe, an emitter, and an optical coupler. The probe has a probe body defining a distal end portion configured for positioning in contact with or close proximity to tissue of interest. The probe further includes an emission optical fiber extending from an input end of the emission optical fiber through the probe body to an output end of the emission optical fiber at the distal end portion of the probe body. The emission optical fiber defines a Numerical Aperture (NA). The emitter is configured to output electromagnetic radiation at a specific wavelength or within a specific wavelength range. The optical coupler optically couples the emitter with the input end of the emission optical fiber such that, in response to receiving the electromagnetic radiation output from the emitter, electromagnetic radiation is input to the input end of the emission optical fiber. The optical coupler is configured to modify the electromagnetic radiation output from the emitter such that the electromagnetic radiation input to the input end of the emission optical fiber defines an NA that is about equal to or less than the NA of the emission optical fiber. In other aspects, the electromagnetic radiation input to the input end of the emission optical fiber defines an NA that is about equal to or less than a predetermined margin (above or below) the NA of the emission optical fiber.

In an aspect of the present disclosure, the NA of the emission optical fiber is equal to about 0.22 such that the NA of the electromagnetic radiation input to the input end of the emission optical fiber is about equal to or less than 0.22. In aspects, the NA is about 0.39, 0.50, or within a range of about 0.22 to about 0.50.

In another aspect of the present disclosure, the optical coupler includes at least one lens. The optical coupler may include at least one collimating lens. Additionally or alternatively, the optical coupler includes a collimator.

In another aspect of the present disclosure, the emitter is a laser.

In still another aspect of the present disclosure, a power of the electromagnetic radiation input to the input end of the emission optical fiber is about 20 mW or about 40 mW and/or the emitter optical fiber defines a core diameter of about 300 μm. Alternatively or additionally, a power of the electromagnetic radiation input to the input end of the emission optical fiber is in conformance with Class 1 or Class 3R per International Electrotechnical Commission (IEC) 60825-1, or within a range of Class 1 through Class 3R of IEC 60825-1.

In yet another aspect of the present disclosure, the tissue detection system further includes a detection optical fiber extending from an output end of the detection optical fiber through the probe body to an input end of the detection optical fiber at the distal end portion of the probe body.

In still yet another aspect of the present disclosure, the tissue detection system further includes a detector operably coupled to the output end of the detection optical fiber.

In another aspect of the present disclosure, in response to the input of the electromagnetic radiation to the input end of the emission optical fiber, the emission optical fiber is configured to output electromagnetic radiation from the output end thereof to stimulate the tissue of interest and the input end of the detection optical fiber is configured to capture fluorescence of the tissue of interest resulting from the stimulation thereof and to transmit the fluorescence to the detector.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIG. 5A is a schematic illustration of still another configuration of a probe, emitter, and detector configured for use with the tissue detection system of FIG. 1;

FIG. 5B is a schematic illustration of one or more optical elements configured for use with the detector of FIG. 5A;

DETAILED DESCRIPTION

In the following description, well-known functions or constructions are not described in detail to avoid obscuring the present disclosure in unnecessary detail. Those skilled in the art will understand that the systems and methods of the present disclosure may be performed by one or more operators "O" (FIG. 1), which may be one or more human clinicians and/or one or more surgical robots.

The tissue detection systems and methods of the present disclosure may be utilized in surgical procedures to identify tissue (via affirmative or negative identification) and, if applicable, facilitate performing a surgical procedure on and/or around the identified tissue. For example, the tissue detection systems and methods of the present disclosure may be utilized to identify parathyroid tissue, thyroid tissue, and/or other tissues in the neck region to facilitate removal or treatment of such tissue or surrounding tissue during surgery. However, although the aspects and features of the present disclosure are described hereinbelow with respect to identifying tissue in the neck region, e.g., parathyroid tissue and/or thyroid tissue, the aspects and features of the present disclosure are equally adaptable for use in the identification of different tissue and/or tissue at different anatomical locations. That is, although different instrumentation may be required to access different tissue and/or different anatomical locations, and although different settings, e.g., different electromagnetic radiation wavelengths, may be required to identify different tissue, the aspects and features of the present disclosure remain generally consistent regardless of the particular instrumentation and/or settings utilized.

Figure 1:
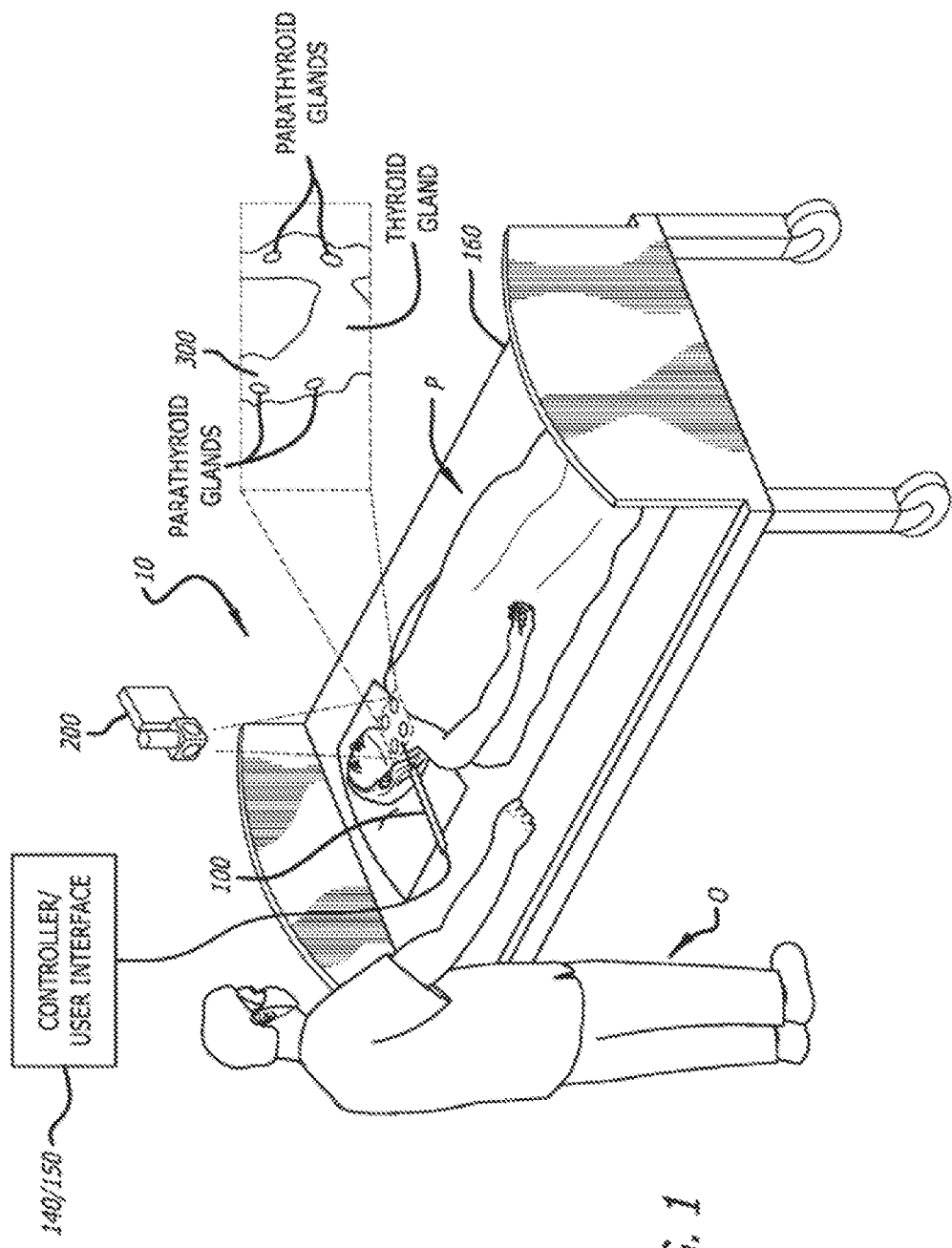
FIG. 1 is a perspective view of a tissue detection system in accordance with the present disclosure illustrated in use in relation to a patient and an operator, where an internal area of the patient is enlarged for reference.

Referring to FIG. 1, a tissue detection system 10 provided in accordance with aspects of the present disclosure generally includes a probe 100, a controller 140, and a user interface 150. In aspects, tissue detection system 10 further includes an external camera system 200 that can include a detector (e.g., an Infrared (IR) camera) to capture fluorescence from fluorescing tissue of interest and/or as standard camera to capture video images. Probe 100 can be positioned by an operator "O" relative to a patient "P" received on a surgical table 160. More specifically, probe 100 is maneuvered into position in contact or close proximity (e.g., within about 5 cm) and directed at tissue of interest such as parathyroid tissue 300 of patient "P." Probe 100 operably connects to one or more emitters 105 (FIG. 2) configured to direct electromagnetic radiation from probe 100 to the tissue of interest to stimulate the tissue of interest such that any fluorescence produced by the stimulated tissue can be detected by one or more detectors 110 (FIG. 2), which may be operably coupled to probe 100, incorporated into or operably coupled to external camera system 200, and/or separately provided.

External camera system 200, in aspects where provided, and as mentioned above, is configured to detect fluorescence and/or to obtain video images. That is, external camera system 200 may include an Infrared (IR) camera and/or a standard video camera. External camera system 200 is positioned spaced-apart from the surgical site as compared to probe 100, such that external camera system 200 provides fluorescence detection and/or video imaging over a relatively large field of view. In aspects, combining use of external camera system 200 with probe 100 enables fluorescence detection by external camera system 200 to identify potentially fluorescing tissue over the relatively large field of view, and enables probe 100 to be used for fluorescence detection locally, within the relatively focused field of view thereof, at the location of each of the potentially fluorescing tissues, e.g., by positioning probe 100 in contact with or in close proximity (e.g., within about 5 cm) to the surface of each of the potentially fluorescing tissue, to enable confirmation as to whether the potentially fluorescing tissue identified by external camera system 200 is indeed fluorescing.

Continuing with reference to FIG. 1, controller 140 and user interface 150 may be incorporated into a single integrated unit, may be physically connected or connectable with one another, or may be separate from one another. Controller 140 and/or user interface 150 can include a display or be connectable to a display, e.g., display 260 (FIGS. 3A and 3B), for displaying information obtained through use of tissue detection system 10 such as, for example, highlighted images of fluorescing tissue and/or video images of tissue.

Controller 140 includes a processor to process data, a memory in communication with the processor to store data, and an input/output unit (I/O) to interface with other modules, units, and/or devices. The processor can include a central processing unit (CPU), a microcontroller unit (MCU), or any other suitable processor or processors. The memory can include and store processor-executable code, which when executed by the processor, configures controller 140 to perform various operations, e.g., such as receiving information, commands, and/or data, processing information and data, and transmitting or providing information/data to another device. To support various functions of controller 140, the memory can store information and data, such as instructions, software, values, images, and other data processed or referenced by the processor. For example, various types of Random-Access Memory (RAM) devices, Read Only Memory (ROM) devices, Flash Memory devices, and other suitable storage media can be used to implement storage functions of the memory. The I/O of controller 140 enables controller 140 to interface with other devices or components of devices utilizing various types of wired or wireless interfaces (e.g., a wireless transmitter/receiver (Tx/Rx)) compatible with typical data communication standards to enable communication between controller 140 and other devices, e.g., user interface 150, display 260 (FIG. 3A), etc. Examples of typical data communication standards include, but are not limited to, Bluetooth®, Bluetooth® low energy, Zigbee®, IEEE 802.11, Wireless Local Area Network (WLAN), Wireless Personal Area Network (WPAN), Wireless Wide Area Network (WWAN), WiMAX®, IEEE 802.16 (Worldwide Interoperability for Microwave Access (WiMAX®)), 3G/4G/LTE cellular communication methods, NFC (Near Field Communication), and parallel interfaces. The I/O of controller 140 can also interface with other external interfaces, sources of data storage, and/or visual or audio display devices, etc. to retrieve and transfer data and information that can be processed by the processor, stored in the memory, and/or output to an external device. In aspects, for example the output may be provided to various types of screen displays, speakers, or printing interfaces, e.g., including but not limited to, LED, liquid crystal display (LCD) monitor or screen, cathode ray tube (CRT), audio signal transducer apparatuses, and/or toner, liquid inkjet, solid ink, dye sublimation, inkless (e.g., such as thermal or UV) printing apparatuses, etc.

User interface 150 may include, for example, any of the output devices noted above, a display, Graphical User Interface (GUI), a touch-screen GUI, a keyboard, a mouse, physical and/or digital buttons, a speaker, one or more LED lights, a foot switch, a hand switch, and/or any other suitable interface devices to enable the input of information, e.g., to control the operation of system 10, and/or to output information, e.g., regarding the status and/or result of the operation of system 10. For example, user interface 150 may: include a suitable input to enable the activation of probe 100, e.g., to emit electromagnetic radiation; include a suitable input (the same or different from the above input) to enable the activation of fluorescence detection, e.g., via probe 100 and/or camera system 200; and/or may provide a perceptible output, e.g., audio, visual, tactile, indicating that a suitable fluorescence signal has been detected.

Figure 2:
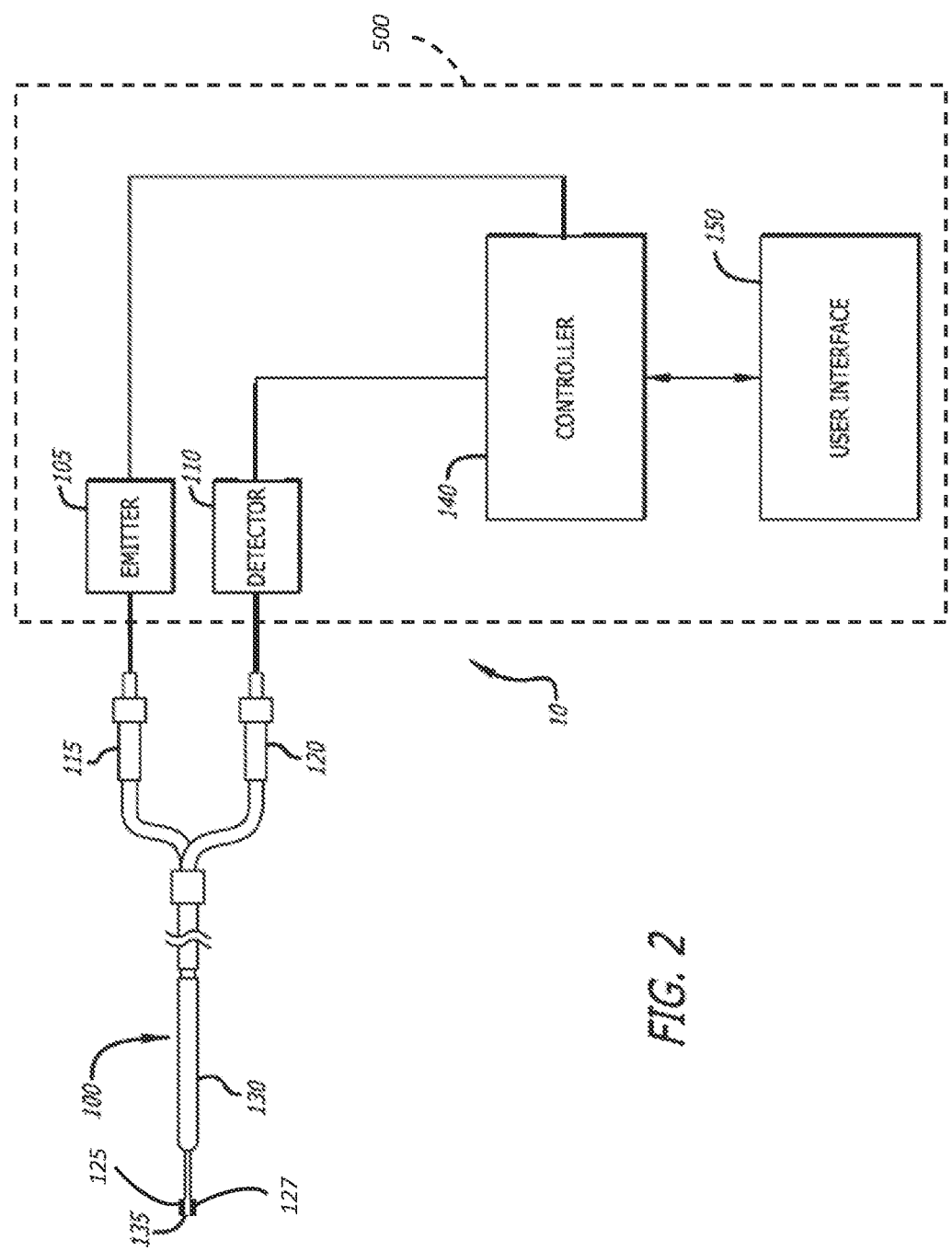
FIG. 2 is a schematic illustration of a probe, emitter, detector, controller, and user interface of the tissue detection system of FIG. 1.

With additional reference to FIG. 2, probe 100, in aspects, may include one or more probe bodies 130 each including one or more emitter optical fiber 115 coupled to one or more emitters 105 and/or one or more detector optical fibers 120 coupled to one or more detectors 110. Additional or alternative detection may be provided by external camera system 200 (FIG. 1). Although plural of the components are contemplated, probe body 130, emitter optical fiber 115, emitter 105, detector optical fiber 120, and detector 110 are described herein below in the singular to facilitate understanding. In aspects, probe 100, or at least probe body 130 thereof, may be integrated (permanently or removably) within a surgical endoscope (not shown) or other surgical device. Emitter 105 and detector 110 may be integrated into a single unit, e.g., a console including a housing, or may be separate from one another. Whether integrated or separate, emitter 105 and/or detector 110 may be integrated with or separate from controller 140 and/or user interface 150. For example, a console 500 may include emitter 105, detector 110, controller 140 and/or user interface 150 incorporated therein or thereon.

Emitter 105 is configured to emit electromagnetic radiation at a particular wavelength or within a particular wavelength range, e.g., via tuning and/or equipment selection, through emitter optical fiber 115 and out a distal end portion 135 of probe body 130 (either axially therefrom, transversely therefrom, or in any other suitable direction or directions including adjustable directions) in order to stimulate fluorescence of a particular tissue or tissues of interest. With respect to identification of parathyroid tissue, for example, emitter 105 (with or without the use of one or more optical elements 125 disposed at the output end of emitter optical fiber 115 at distal end portion 135 of probe body 130) may be configured to emit electromagnetic radiation in the form of laser energy at a wavelength of about 785 nm to facilitate auto-fluorescence of parathyroid tissue. Emitter 105, at least for use in identifying parathyroid tissue, may be a narrow band source such as a laser (e.g., a solid state laser, a laser diode, etc.) or other suitable source whose electromagnetic radiation output wavelength is at or near a narrow band around about 785 nm. Tuning, equipment selection, and/or filtering (using one or more optical elements 125, e.g., a band-pass (BP) filter, disposed at the output end of emitter optical fiber 115 at distal end portion 135 of probe body 130) may be utilized to facilitate achieving this narrow band. Of course, for identification of different tissues, different narrow (or broader) wavelength bands may be utilized and, as a result, different tuning, equipment selection, and/or optical elements 125 may be provided. Optical elements 125 may alternatively or additionally be disposed at different locations other than at distal end portion 135 of probe body 130 and may include, for example, lenses, filters, mirrors, beamsplitters, etc. Controller 140 can be used to control transmission, e.g., activate/deactivate, control the wavelength, intensity, etc., of the electromagnetic radiation from emitter 105 to tissue of interest (via emitter optical fiber 115). User interface 150 can be used to interact with and control operation of the controller 140 (e.g., to set parameters and/or activate/deactivate), which in turn controls emitter 105.

Detector 110 is configured to detect fluorescence of the tissue of interest (as a result of the electromagnetic radiation emitted to stimulate the tissue of interest) collected at distal end portion 135 of probe body 130 and transmitted through detector optical fiber 120 to detector 110. Detector 110 is further configured to process the received fluorescence signal. Controller 140 may be utilized to control and/or facilitate processing of the detected fluorescence signal at detector 110. With respect to identification of parathyroid tissue, detector 110 may be configured to process the fluorescence signal, which for parathyroid tissue undergoing auto-fluorescence is at wavelengths ranging from about 808 nm to about 1000 nm. Detector 110 may be an avalanche photodiode or other near IR detector, a 2D array of IR detectors, or other suitable detector, and may be used in concert with one or more optical elements 127, e.g., a longpass (highpass) optical filter, such that radiation wavelengths above the source wavelength (for instance, above about 800 nm, e.g., ranging from about 808 to about 1000 nm) can be detected with minimal interference from other non-relevant wavelengths of electromagnetic radiation, e.g., such as from ambient light. Reducing the effects of ambient light may also be accomplished by positioning probe body 135 in contact with or close proximity (e.g., within about 5 cm) to the tissue of interest during emission/detection; by modulating the emitter radiation; and/or by collecting the fluorescence signal using a phase lock technique, e.g., lock-in detection or FFT (fast Fourier transform) techniques. With respect to the one or more optical elements 127 (such as a Long-Pass (LP) filter, for example), such optical elements 127, in aspects, are provided at the input end of detector optical fiber 120 at distal end portion 135 of probe body 130. Alternatively or additionally, the one or more optical elements 127 may be disposed at the input to detector 110, e.g., at the output end of detection optical fiber 120 or between the output end of detection optical fiber 120 and the input to detector 110.

A detected fluorescence signal, e.g., obtained by detector 110, for a tissue of interest may be processed by comparison with a threshold fluorescence signal to determine if the detected fluorescence signal is indicative of the presence of a particular tissue, or may be processed in any other suitable manner. Details with respect to systems and methods using auto-fluorescence for discriminating parathyroid tissue from thyroid tissue or other tissues in a neck region are described in U.S. Pat. No. 9,687,190 titled "Intra-Operative Use of Fluorescence Spectroscopy and Applications of Same," the entire contents of which are hereby incorporated by reference herein. As disclosed therein, when the thyroid and the parathyroid tissue are exposed to radiation in a narrow wavelength range of about 785 nm, which is just outside the visible light range, both the thyroid and the parathyroid tissue auto-fluoresce in a wavelength range above about 800 nm, sometimes centered at about 822 nm (the wavelength range above about 800 nm is also not visible). However, the intensity of the fluorescence of the parathyroid tissue is significantly higher than that of the thyroid material, thus enabling distinction between these two tissues.

Figure 3B:
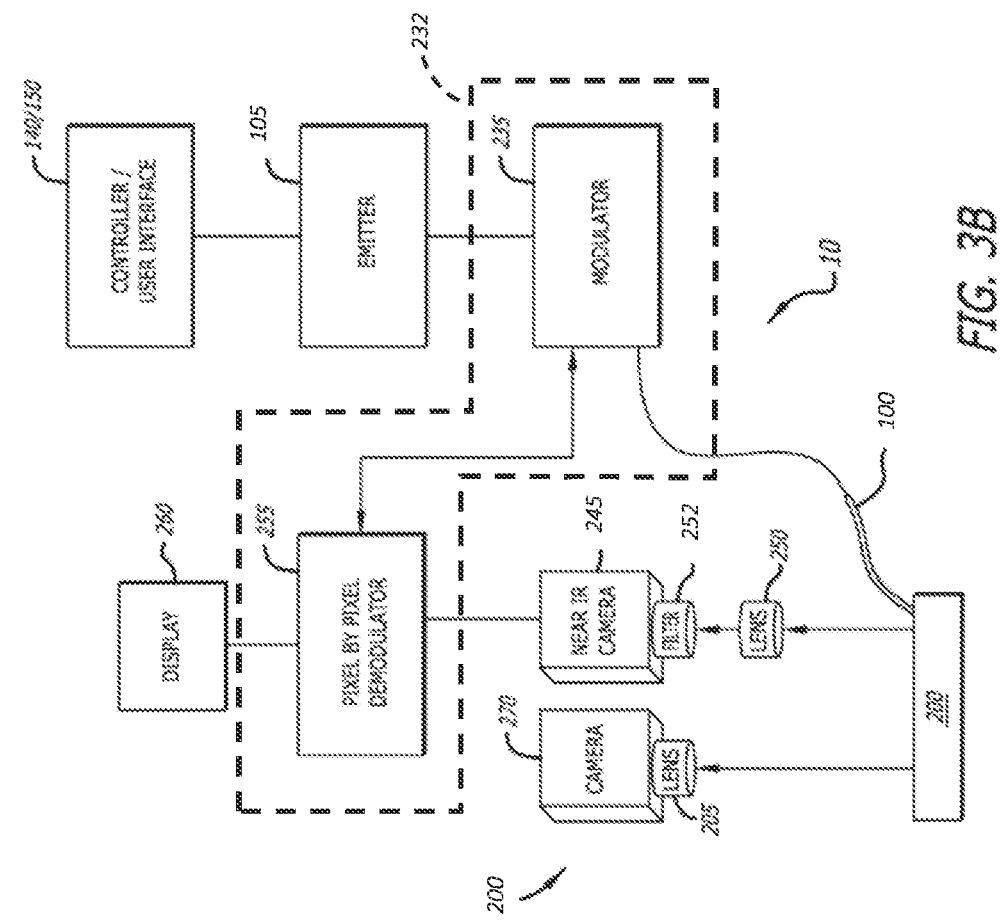
FIG. 3B is a block diagram of the tissue detection system of FIG. 1 including a near infrared camera with pixel by pixel demodulation and a standard video camera.
Figure 3A:
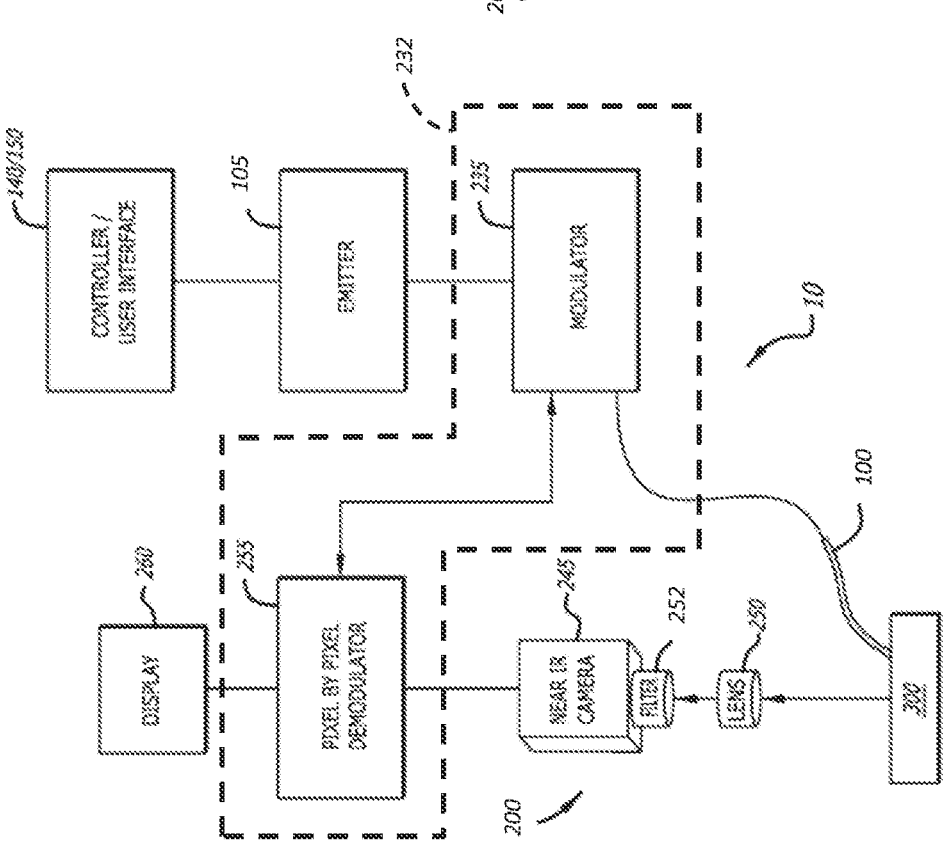
FIG. 3A is a block diagram of the tissue detection system of FIG. 1 including a near infrared camera with pixel by pixel demodulation.

Turning to FIGS. 3A and 3B, and initially with reference to FIG. 3A, system 10 is shown wherein camera system 200 functions as at least one detector of the system and includes a near IR camera 245 and one or more optical elements, e.g., one or more lens 250 and/or one or more filters 252, positioned to modify the fluorescence signal to be received by near IR camera 245. Further, a display 260, which may be configured as any of the above-noted output devices, above-noted user interface devices, or any other suitable device for displaying information, is provided. As noted above, display 260 can be separate from or integrated with controller 140 and/or user interface 150, e.g., incorporated into or connected with console 500 (FIG. 2).

System 10 as shown in FIG. 3A may further include, in aspects, a modulation and demodulation sub-system 232 including a modulator 235 to alter the emitted radiation wavelength, e.g., lower or higher, from emitter 105. Modulator 235 may be, for example, a chopper, pockel cell, acoustic optical modulator, or other suitable light modulation device or combination of devices. The modulated emitter signal is provided to probe 100 which, in turn, provides the modulated emitter signal to the tissue of interest, e.g., parathyroid tissue 300.

Near IR camera 245, with or without use of optical elements 250, 252 captures any fluorescence radiation (e.g., resulting from the stimulation of the tissue of interest by the emitted electromagnetic radiation provided by emitter 105 via probe 100) within its field of view, which includes the tissue of interest. In aspects where modulation and demodulation sub-system 232 is provided, the fluorescence signal obtained by near IR camera 245 may be passed through a demodulator 255 of sub-system 232, which can use a modulator frequency from modulator 235 as an input, to produce a demodulated signal that is transmitted from demodulator 255 to display 260.

Demodulator 255, in aspects where provided, may be configured to demodulate successive frames of images from near IR camera 245 in pixel by pixel fashion. Such pixel by pixel demodulation may include digital lock-in to the modulation frequency, or (fast) Fourier transform demodulation. In aspects, modulation and demodulation sub-system 232 is omitted, or other suitable modulation and demodulation components are utilized.

The output from demodulator 255 (where provided) or from near IR camera 245 (where modulation and demodulation sub-system 232 is omitted) is a fluorescence signal that is transmitted to display 260. More specifically, successive demodulated video frames may be continuously provided to display 260 from demodulator 255, thus resulting in the substantially real time display of demodulated video images of any fluorescing tissue including an indication of the wavelength and/or intensity of such fluorescence, e.g., via highlighting, color change, or in any other suitable manner. Similar video frames may be provided from near IR camera 245 to provide a similar result without the use of demodulator 255.

With respect to the configuration of FIG. 3A, detailed above, in addition to detection camera system 200 functioning as a detector, e.g., via near IR camera 245, detection may also be provided by detector 110 via probe 100, as detailed above with reference to FIG. 2. Such detection may be performed similarly as detailed above, with or without a sub-system like sub-system 232, and the results may be displayed on display 260 or a different display in a similar manner.

Referring to FIG. 3B, system 10 is shown similarly as detailed above with respect to FIG. 3A except that camera system 200 includes, in addition to near IR camera 245, a standard video camera 270 (that can employ one or more optical elements such as a lens 205). Camera system 200 may include IR camera 245 and standard video camera 270 integrated into a single unit, connected to or connectable with one another, or these cameras 245, 270 may be separate from one another.

Near IR camera 245 and standard video camera 270 may be configured to image overlapping and, in aspects, coextensive fields of view. Near IR camera 245 can be used, as detailed above, as a detector to capture a fluorescence signal from fluorescing tissue of interest. Further, in aspects where sub-system 232 is provided, pixel lock-in or other demodulation may be performed on the output from near IR camera 245 by the demodulator 255. Demodulated pixels from near IR camera 245 that meet certain criteria can be matched with corresponding output pixels from the standard video camera 270 to enable highlighting of fluorescing tissue (as detected by near IR camera 245) on the video images produced by standard video camera 270. The highlighted video image may ultimately be displayed on display 260 and/or another suitable display such that the highlighted tissue on the substantially real-time video image can be readily identified. Other suitable techniques for highlighting fluorescing tissue on substantially real-time video images, overlaying fluorescing tissue images onto substantially real-time video images, or otherwise indicating fluorescing tissue on substantially real-time video images may also be provided.

With respect to the configuration of FIG. 3B, detailed above, in addition to detection camera system 200 functioning as a detector, e.g., via near IR camera 245, detection may also be provided by detector 110 probe 100, as detailed above with reference to FIG. 2. Such detection may be performed similarly as detailed above, with or without a sub-system like sub-system 232, and the results may be displayed on display 260 or a different display. In other aspects, camera system 200 only includes standard video camera 270 with all detection being provided by detector 110 via probe 100, as detailed above with reference to FIG. 2.

Methods of calibration and use suitable for system 10 (FIG. 1) are detailed in Patent Application Publication No. US 2020/0305696 titled "Tissue Detection System and Methods for use Thereof," the entire contents of which are hereby incorporated by reference herein.

Referring back to FIG. 2, in aspects, one or more optical elements 125 such as, for example, a Band-Pass (BP) filter, may be disposed at distal end portion 135 of probe body 130. The BP filter modifies the electromagnetic radiation emitted from the output end of emitter optical fiber 115 and, more specifically, eliminates unwanted fluorescence from the emission. Without controlling the Numerical Aperture (NA) of the electromagnetic radiation, e.g., laser energy, entering emitter optical fiber 115, monochromatic laser light energy at angles larger than the NA of emitter optical fiber 115 may make fiber 115 fluoresce and, if not eliminated, this fluorescence may be detected as false positives when evaluating whether the tissue of interest fluoresces. This may occur where the power of the electromagnetic radiation emission produced by emitter 105, e.g., a laser, and provided at the input end of emitter optical fiber 115 is relatively large and at relatively large angles while emitter optical fiber 115 is relatively small and defines a relatively small NA. For example, the power of the electromagnetic radiation at the input end of emitter optical fiber 115 may be about 20 mW or about 40 mW (or any other suitable power) while emitter optical fiber 115 may be an about 300 μm core diameter fiber (although other diameters are also contemplated) with an NA of about 0.22, 0.39, 0.50, or within a range of about 0.22 to about 0.50. Other NA's are also contemplated. In aspects, the power of the electromagnetic radiation at the input end of emitter optical fiber 115 is in conformance with Class 1 or Class 3R per International Electrotechnical Commission (IEC) 60825-1, or within a range of Class 1 through Class 3R of IEC 60825-1. In the above and other configurations, fluorescence of the emitter optical fiber 115 will occur. Providing the BP filter at distal end portion 135 of probe body 130 eliminates this unwanted fluorescence and, thus, reduces the likelihood of false positives.

Figure 4:
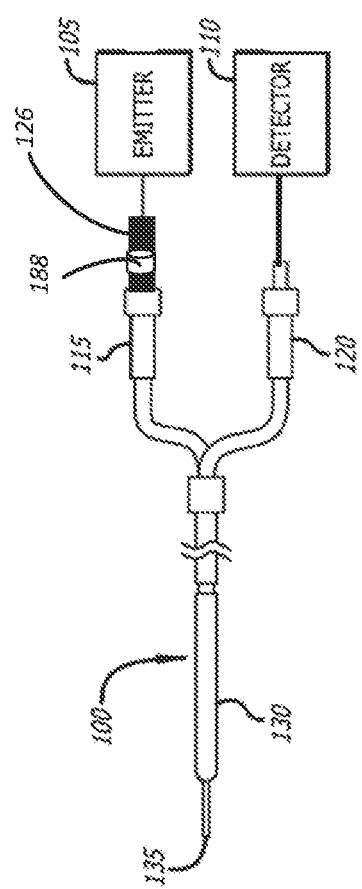
FIG. 4 is a schematic illustration of another configuration of a probe, emitter, and detector configured for use with the tissue detection system of FIG. 1.

Turning to FIG. 4, as an alternative to providing an optical element 125 (FIG. 2) in the form of a BP filter (or other suitable optical element) at distal end portion 135 of probe body 130 (at the output end of emission optical fiber 115) to eliminate unwanted fluorescence, an optical coupler 126 may be provided at the input end of emission optical fiber 115 to control the NA of the electromagnetic radiation entering emission optical fiber 115, thus eliminating or reducing fluorescence of emission optical fiber 115. More specifically, the NA of the electromagnetic radiation entering emission optical fiber 115 may be controlled by the optical coupler 126 to not exceed the NA of emission optical fiber 115 or to not exceed a pre-determined margin above the NA of emission optical fiber 115, e.g., wherein the NA of the electromagnetic radiation is controlled to not exceed 5% above the NA of emission optical fiber 115, 10% above, or 15% above. Control may alternatively be provided such that the NA of the electromagnetic radiation entering emission optical fiber 115 does not exceed a pre-determined margin below the NA of emission optical fiber 115, e.g., wherein the NA of the electromagnetic radiation is controlled to not exceed 5% below the NA of emission optical fiber 115, 10% below, or 15% below. By controlling the NA of the electromagnetic radiation entering emission optical fiber 115 to below or minimally above the NA of emission optical fiber 115 as detailed above, the electromagnetic radiation within emission optical fiber 115 will achieve or at least approach Total Internal Reflection (TIR) and, thus, inhibit or reduce fluorescence of emission optical fiber 115. In aspects, the NA of emission optical fiber 115 is about 0.22 and optical coupler 126 controls the NA of the electromagnetic radiation to emission optical fiber 115 to at, below, or minimally above 0.22.

The optical coupler 126 may include a collimator and/or may have, for example, one or more lenses 188 (e.g., a single aspheric lens, an anamorphic lens pair, or an aspheric lens and anamorphic prisms, or any other suitable lens(es)); an aperture; and/or any other suitable optical elements. As an alternative to or in addition to optical coupler 126 controlling the NA, emitter 105 (e.g., a laser) may be controlled, e.g., by controlling beam width diameter, to control the NA of the electromagnetic radiation provided at the input end of emission optical fiber 115 to at, below, or minimally above the NA of emission optical fiber 115. Configuring the emitter 105 itself and/or providing optical coupler 126 configured as detailed above enables matching (exact matching or within the above-noted ranges) of the NA of the electromagnetic radiation at the input end of emission optical fiber 115 with the NA of emission optical fiber 115, e.g., 0.22, thus reducing or inhibiting fluorescence of emission optical fiber 115.

Referring back to FIG. 2, as noted above, one or more optical elements 127, e.g., an LP filter, may be provided at the input end of detector optical fiber 120 at distal end portion 135 of probe body 130 and/or at the input to detector 110 (e.g., at the output end of detector optical fiber 120) to filter out the electromagnetic radiation such that only relevant fluorescent radiation wavelengths are detected. For parathyroid tissue, for example, which undergoes autofluorescence at wavelengths ranging from about 808 nm to about 1000 nm, the LP filter (or other suitable optical element(s) 127) may thus be configured to filter out wavelengths other than those above about 800 nm (e.g., ranging from about 808 nm to about 1000 nm), thus facilitating detection of the relevant electromagnetic radiation at wavelengths above about 800 nm (or ranging from about 808 nm to about 1000 nm).

With reference to FIGS. 5A and 5B, as an alternative to providing an LP filter at the input end of detector optical fiber 120 at distal end portion 135 of probe body 130, suitable optics 128, e.g., one or more optical elements 128, may be provided at or within detector 110 (and/or within a console including detector 110, e.g., console 500 (FIG. 2), if so provided). Such optics 128 may include, for example, a fiber optic shunt such as, for example, an LP filter 129a and, in aspects, an input 129b, e.g., an input fiber, and/or an output 129c, e.g., an output fiber. Optics 128 are positioned in series with detector optical fiber 120 and other optics associated with detector 110 (or otherwise provided in the console e.g., console 500 (FIG. 2), if so provided). Optics 128 provide similar optical performance as including the LP filter at the input end of detector optical fiber 120 at distal end portion 135 of probe body 130 (see FIG. 2). However, providing optics 128 in detector 110 (and/or console 500 (FIG. 2)) enables the optics 128 to be moved to more capital equipment, e.g., the console, as compared to more consumable equipment, e.g., the probe, and also places optics 128 in a much less space-confined portion of system 10 (FIG. 1), thus providing more options and/or configurations for implementing optics 128 in a manner that filters out the electromagnetic radiation such that only relevant fluorescent radiation wavelengths are detected.

Figure 6:
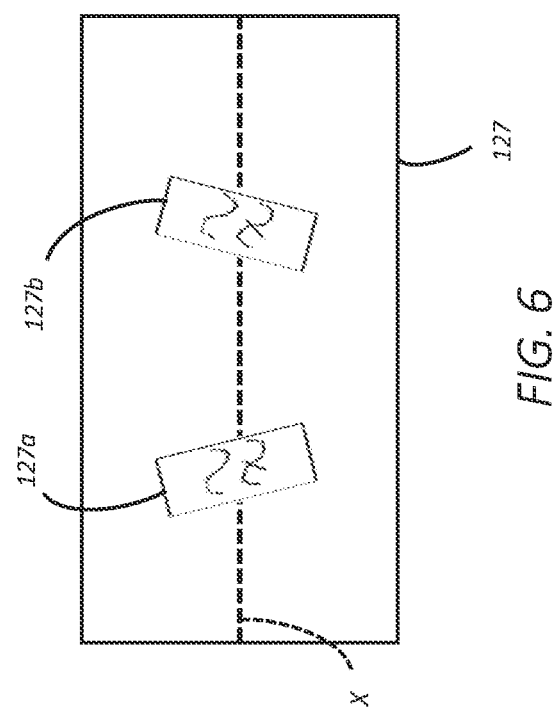

Turning to FIG. 6, in conjunction with FIG. 2, the one or more optical elements 127 provided at the input end of detector optical fiber 120 at distal end portion 135 of probe body 130 or at the input to detector 110 to filter out the electromagnetic radiation such that only relevant radiation wavelengths are detected may include, for example, a first filter 127a and a second filter 127b disposed at a tilt angle relative to one another. Either or both filters 127a, 127b may be disposed at a tilt angle relative to the optical axis "X," or one of the filters 127a, 127b may be perpendicularly arranged relative to optical axis "X." First and second filters 127a, 127b may be LP filters or any other suitable filters. By providing first and second filters 127a, 127b in this relatively tilted manner, the Optical Density (OD) provided by the filters 127a, 127b can be increased. In aspects, the OD of each filter 127a, 127b individually is about 6 or less, whereas the OD provided by the relatively tilted filters 127a, 127b together is, in aspects, at least about 9; and in other aspects, at least about 12.

Figure 7:
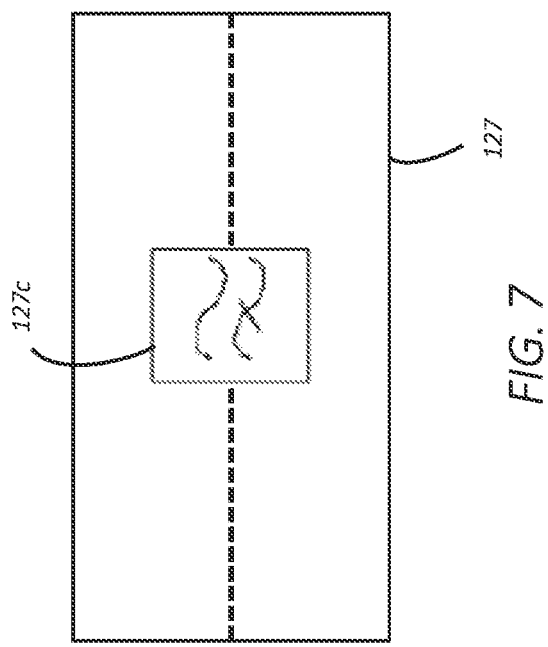
FIGS. 6 and 7 are schematic illustrations of one or more optical elements configured for use with the probe of FIG. 2.

Referring to FIG. 7, in conjunction with FIG. 2, the one or more optical elements 127 provided at the input end of detector optical fiber 120 at distal end portion 135 of probe body 130 and/or at the input to detector 110 (e.g., at the output end of detector optical fiber 120) to filter out the electromagnetic radiation such that only relevant radiation wavelengths are detected may alternatively include, for example, a custom filter 127c having an OD of, in aspects, at least about 9; in other aspects from about 9 to about 12; and in still other aspects, of at least about 12. These ODs provided by custom filter 127c are significantly greater than the ODs of currently available off-the-shelf filters suitable for use at distal end portion 135 of probe body 130. Such off-the-shelf filters provide a maximum OD of about 6. Custom filter 127c may be formed, for example, as a reflective metallic thin film optical coating applied to a glass substrate (such filters are also referred to as ND filters).

Figure 8:
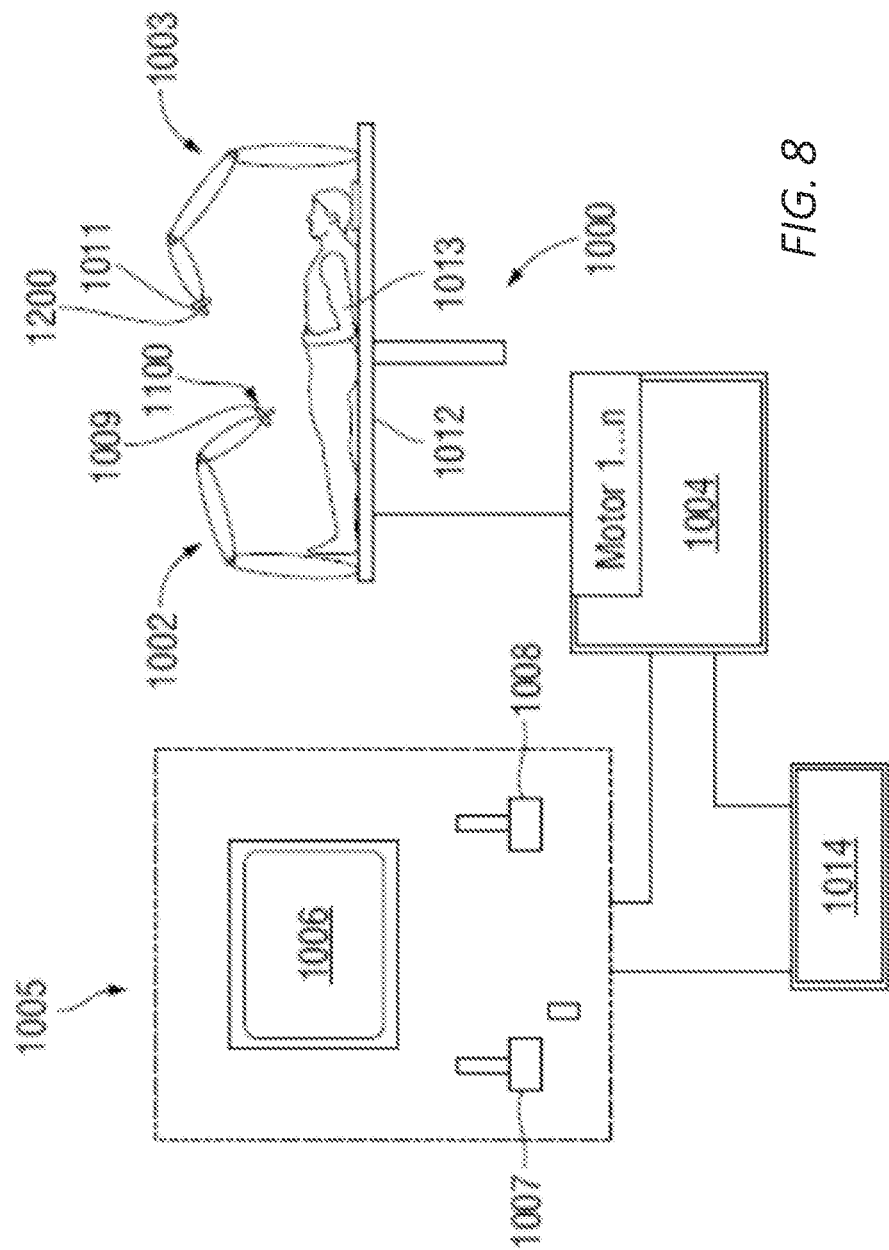
FIG. 8 is a schematic illustration of a robotic surgical instrument configured for use in accordance with the present disclosure.

Turning to FIG. 8, as noted above, the tissue detection systems and methods of the present disclosure may be at least partially implemented by a surgical robot operator "O" (FIG. 1) such as robotic surgical instrument 1000 provided in accordance with the present disclosure. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in an operating mode. Robotic surgical instrument 1000 may be configured for use on a patient 1013 lying on a patient table 1012. Robotic surgical instrument 1000 may further include or be capable of accessing a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100, for example, may be a probe 100 (FIG. 1) in accordance with the present disclosure such that, together with robot arm 1002, probe 100 (FIG. 1) may be manipulated and/or operated similarly as detailed above except in a robotically-actuated and controlled manner. Likewise, end effector assembly 1200 may be surgical camera 200 (FIG. 1) in accordance with the present disclosure such that, together with robot arm 1003, external camera 200 (FIG. 1) may be manipulated and/or operated similarly as detailed above except in a robotically-actuated and controlled manner. Other suitable end effector assemblies for coupling to attaching devices 1009, 1011 are also contemplated. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:

1. A tissue detection system, comprising:
   a probe having a probe body defining a distal end portion configured to be placed in contact with or in close proximity to tissue of interest, the probe including an emission optical fiber extending from an input end of the emission optical fiber through the probe body to an output end of the emission optical fiber at the distal end portion of the probe body and a detection optical fiber extending from an output end of the detection optical fiber through the probe body to an input end of the detection optical fiber at the distal end portion of the probe body;
   an emitter coupled to the input end of the emission optical fiber and configured to generate electromagnetic (EM) radiation;
   a detector coupled to the output end of the detection optical fiber;
   a near infrared (IR) camera configured to image fluorescence radiation resulting from delivery of the EM radiation to tissue via the emission optical fiber;
   a modulator configured to alter the EM radiation generated by the emitter; and
   a demodulator configured to:
      demodulate successive frames of images received from the near IR camera based on a modulator frequency received from the modulator; and
      continuously output, based on the successive frames of images, successive demodulated video frames to a display for visualizing demodulated video images of fluorescing tissue in real time.

2. The tissue detection system according to claim 1, further comprising first and second optical elements configured to filter out electromagnetic radiation received from the detection optical fiber below a pre-determined wavelength threshold or outside of a pre-determined wavelength range.

3. The tissue detection system according to claim 1, further comprising first and second optical elements configured to filter out electromagnetic radiation below a pre-determined wavelength threshold of about 800 nm.

4. The tissue detection system according to claim 1, further comprising first and second optical elements configured to filter out electromagnetic radiation outside of a pre-determined wavelength range of about 808 to about 1000 nm.

5. The tissue detection system according to claim 1, wherein the probe does not include a filter disposed on an input side of the detection optical fiber.

6. The tissue detection system according to claim 1, wherein the emitter is configured to input electromagnetic radiation to the input end of the emission optical fiber at a wavelength of about 785 nm.

7. A tissue detection system, comprising:
   a probe having a probe body defining a distal end portion configured to be placed in contact with or in close proximity to tissue of interest, the probe including an emission optical fiber and a detection optical fiber;
   an emitter coupled to the emission optical fiber and configured to generate electromagnetic (EM) radiation;
   a detector including an input coupled to an output end of the detection optical fiber;
   a near infrared (IR) camera configured to image fluorescence radiation resulting from delivery of the EM radiation to tissue via the emission optical fiber;
   a modulator configured to alter the EM radiation generated by the emitter; and
   a demodulator configured to:
      demodulate successive frames of images received from the near IR camera based on a modulator frequency received from the modulator; and
      continuously output, based on the successive frames of images, successive demodulated video frames to a display for visualizing demodulated video images of fluorescing tissue in real time.

8. The tissue detection system according to claim 7, further comprising first and second filters configured to filter out electromagnetic radiation received from the detection optical fiber below a pre-determined wavelength threshold or outside of a pre-determined wavelength range.

9. The tissue detection system according to claim 7, further comprising first and second filters, wherein at least one of the first or second filters is angled relative to an optical axis of the detection optical fiber.

10. The tissue detection system according to claim 7, further comprising first and second filters defining a collective Optical Density (OD) of at least about 9 without any one of the first or second filters defining an individual OD of more than about 6.

11. The tissue detection system according to claim 7, further comprising first and second filters defining a collective Optical Density (OD) of at least about 12 without any one of the first or second filters defining an individual OD of more than about 6.

12. The tissue detection system according to claim 7, further comprising first and second filters configured to filter out electromagnetic radiation below a pre-determined wavelength threshold of about 800 nm.

13. The tissue detection system according to claim 7, further comprising first and second filters configured to filter out electromagnetic radiation outside of a pre-determined wavelength range of about 808 to about 1000 nm.

14. A tissue detection system, comprising:
a probe including an emission optical fiber having an output end at the distal end portion of the probe body and a detection optical fiber having an input end at the distal end portion of the probe body;
an emitter coupled to an input end of the emission optical fiber and configured to generate electromagnetic (EM) radiation;
a detector including an input coupled to an output end of the detection optical fiber;
a near infrared (IR) camera configured to image fluorescence radiation resulting from delivery of the EM radiation to tissue via the emission optical fiber;
a modulator configured to alter the EM radiation generated by the emitter; and
a demodulator configured to:
demodulate successive frames of images received from the near IR camera based on a modulator frequency received from the modulator; and
continuously output, based on the successive frames of images, successive demodulated video frames to a display for visualizing demodulated video images of fluorescing tissue in real time.

15. The tissue detection system according to claim 14, further comprising a single filter defining an OD of at least about 12.

16. The tissue detection system according to claim 14, further comprising a Long-Pass (LP) filter.

17. The tissue detection system according to claim 14, further comprising a single filter configured to filter out electromagnetic radiation below a pre-determined wavelength threshold of about 800 nm.

18. The tissue detection system according to claim 14, further comprising a single filter configured to filter out electromagnetic radiation outside of a pre-determined wavelength range of about 808 to about 1000 nm.

* * * * *